(12) United States Patent
Houston et al.

(10) Patent No.: US 7,503,226 B2
(45) Date of Patent: Mar. 17, 2009

(54) METHOD OF AND APPARATUS FOR ASSESSING THE EFFECT OF A CONDUIT SECTION ON FLOW CHARACTERISTICS OF A FIRST FLUID

(75) Inventors: John Graeme Houston, Perth (GB);
Peter Arno Stonebridge, Perth (GB);
John Bruce Cameron Dick, Coupar Angus (GB); Robert Gordon Hood, Perth & Kinross (GB); Allana Johnstone, Dunblane (GB); Christophe Emmanuel Sarran, Perth (GB); Craig McLeod Duff, Dundee (GB)

(73) Assignee: Tayside Flow Technologies Ltd, Dundee (GB)

( * ) Notice: Subject to any disclaimer, the term of this patent is extended or adjusted under 35 U.S.C. 154(b) by 486 days.

(21) Appl. No.: 10/492,431

(22) PCT Filed: Sep. 18, 2002

(86) PCT No.: PCT/GB02/04243

§ 371 (c)(1),
(2), (4) Date: Mar. 17, 2005

(87) PCT Pub. No.: WO03/024334

PCT Pub. Date: Mar. 27, 2003

(65) Prior Publication Data

US 2005/0165289 A1    Jul. 28, 2005

(30) Foreign Application Priority Data

Sep. 18, 2001  (GB) .................................. 0122476.5

(51) Int. Cl.
*G01F 1/86*       (2006.01)
*A61B 8/00*       (2006.01)

(52) U.S. Cl. ............ 73/861.351; 73/61.73; 73/861.356; 600/437

(58) Field of Classification Search ............ 73/861.352, 73/861.354, 861.355, 861.356, 861.357, 73/861.42, 54.24, 54.41, 861.351, 961.354, 73/861.01, 61.73; 600/437, 453–456
See application file for complete search history.

(56) References Cited

U.S. PATENT DOCUMENTS 5,365,795 A * 11/1994 Brower, Jr. ............... 73/861.65

(Continued)

FOREIGN PATENT DOCUMENTS

EP    1234554 A1    8/2002

(Continued)

OTHER PUBLICATIONS

D.H. Evans et al., "Doppler Ultrasound: Physics, Instrumentation and Signal Processing," 2000, pp. 325-333, John Wiley, Chichester, England.

*Primary Examiner*—Hezron Williams
*Assistant Examiner*—J M Saint Surin
(74) *Attorney, Agent, or Firm*—DeMont & Breyer LLC

(57) ABSTRACT

A method of assessing the effect of a conduit section (11) on flow characteristics of a first fluid in a first conduit system (1). A first fluid is caused to flow through the first conduit system (1). A transverse flow parameter of the first fluid in the first conduit system (1) downstream of the conduit section (11) is detected. At least one transverse flow characteristic of the first fluid is determined from the detected transverse flow parameter. The effect of the conduit section (11) is then assessed from the determined flow characteristics.

19 Claims, 3 Drawing Sheets

U.S. PATENT DOCUMENTS

| | | | |
|---|---|---|---|
| 5,861,561 A * | 1/1999 | Van Cleve et al. | 73/861.52 |
| 5,967,986 A | 10/1999 | Cimochowski et al. | |
| 6,030,344 A * | 2/2000 | Guracar et al. | 600/447 |
| 6,151,557 A * | 11/2000 | Broden et al. | 702/47 |
| 6,463,810 B1 * | 10/2002 | Liu | 73/861.63 |
| 6,464,640 B1 * | 10/2002 | Guracar et al. | 600/453 |
| 6,535,835 B1 * | 3/2003 | Rubin et al. | 702/159 |
| 6,547,731 B1 * | 4/2003 | Coleman et al. | 600/455 |
| 6,609,431 B1 * | 8/2003 | Tietsworth et al. | 73/861.52 |
| 6,715,339 B2 * | 4/2004 | Bonne et al. | 73/24.01 |
| 6,971,259 B2 * | 12/2005 | Gysling | 73/32 A |

FOREIGN PATENT DOCUMENTS

| | | |
|---|---|---|
| FR | 2779340 A | 12/1999 |
| WO | WO-9858599 A | 12/1998 |
| WO | WO-0038591 A | 7/2000 |

* cited by examiner

METHOD OF AND APPARATUS FOR ASSESSING THE EFFECT OF A CONDUIT SECTION ON FLOW CHARACTERISTICS OF A FIRST FLUID

This invention relates to a method of and apparatus for assessing the effect of a conduit section on flow characteristics of a first fluid.

WO 00/38591 discloses the use of tubing, for example, blood flow tubing, with internal spiral formations to improve flow through the tubing is at least some respects. In particular, spiral flow induced by a spiral formation in an artery or graft can reduce or eliminate dead flow regions and turbulence, leading to reduced tendency of stenosis. The same effect is observed in industrial tubing and pipes.

The effect depends upon the dimensions of the tubing and the properties of the fluid flow, its density, viscosity and its speed, as well as on the nature of the spiral formation.

For a given fluid flow, the problem is to specify an internal spiral formation, of a tube of given dimensions, that produces a beneficial effect; a further problem is to specify a formation which optimises the effect. Given all the possible variations in tube dimensions and fluid properties, as well as the number of different ways in which a spiral formation can be realised, and given the difficulty of even observing spiral flow, especially in narrow bore tubing, the trial and error approach is often tedious, and cannot ever be guaranteed to produce the best design, since there will always be some configurations that remain unexplored.

The term "spiral" as used herein covers the mathematical definitions of spiral, helical or a combination of spiral and helical.

In accordance with a first aspect of the present invention, there is provided a method of assessing the effect of a conduit section on flow characteristics of a first fluid in a first conduit system, the method comprising:
  (a) causing a first fluid to flow through the first conduit system;
  (b) detecting a transverse flow parameter of the first fluid in the first conduit system;
  (c) determining at least one transverse flow characteristic of the first fluid from the detected transverse flow parameter; and
  (d) assessing the effect of the conduit section from the determined flow characteristics.

In accordance with a second aspect of the present invention, there is provided apparatus for assessing the effect of a conduit section on flow characteristics of a first fluid in a first conduit system, the apparatus comprising:
  (a) a sensing system mounted adjacent to a detecting region of the first conduit system, the sensing system generating an output signal representative of a transverse flow parameter in the detecting region;
  (b) a processor for receiving the output signal and processing the output signal to derive at least one transverse flow characteristic of the first fluid from the output signal; and
  (c) a display device to display the at least one flow characteristic.

Typically, the transverse flow parameter is detected downstream of the conduit section.

Preferably, the transverse flow parameter comprises transverse flow velocity, and typically, a number of transverse flow velocities are detected across a cross-section of the first conduit system.

Typically, the transverse flow parameter is detected using ultrasound, and preferably, using a Döppler ultrasound technique. However, other detection methods are possible, such as magnetic resonance imaging (MRI).

Preferably, the at least one transverse flow characteristic that is determined comprises a quantitative flow characteristic. Typically, the quantitative flow characteristic comprises one or more of peak transverse flow velocity and spiral statistical uncertainty.

Preferably, the at least one transverse flow characteristic that is determined comprises a qualitative flow characteristic. Typically, the qualitative flow characteristic comprises one or more of transverse flow profile and transverse velocity profile.

Typically, the pressure of the first fluid in the flow system is also detected. The pressure may be detected upstream and/or downstream of the conduit section.

The conduit section may comprise an internal spiral formation.

In one example of the invention, the invention may be used to assess the effect of the conduit section on the flow characteristics of a second fluid in a second conuit system. In this example, initially flow characteristics of the second conduit system are analysed, the first conduit system is configured to at least partially emulate the second conduit system, and a second assessment of the effect of the conduit section on the flow characteristics of a second fluid in the second conduit system are derived from the assessment of the effect of the conduit section on the flow characteristics of the first fluid in the first conduit system. Preferably, the first fluid has a known relationship to the second fluid.

Preferably, the detecting region is a cross-section of the first conduit system.

Typically, the sensing system comprises a source of ultrasonic waves and a sensor for detecting ultrasonic waves from the detecting region of the first conduit system. Alternatively, the sensing system may comprise any other suitable sensing system, such as an MRI system.

Preferably, the first and second fluids are liquids. The first conduit system may comprise upstream and downstream tubing delivering fluid to and receiving if from the conduit section. The upstream tubing may be such as deliver specific amounts of turbulence in the flow and non-rotational flow to the conduit section, and the downstream tubing may be such as not to induce turbulence and/or rotation which could be propagate upstream. Smooth-walled tubing, such as silicon or silicon-lined or silicone treated tubing will usually be found suitable.

The first conduit system may comprise a source for the fluid and pressure means to provide a pressure head in the fluid. The pressure means may comprise a fluid reservoir elevated above the tube, and/or a pump.

Usually, the fluid will be a liquid. For testing blood flow tubing, the fluid will be blood, or, preferably, a liquid simulating blood, as by having comparable density and viscosity. For Döppler ultrasound measurements, the fluid may also have comparable acoustic refractive index.

The effect of a stenosis may be observed by making measurements with and without such. An apertured plug may be inserted in the downstream tube of a flow system for this. Testing the effect of different stenosis values (stenosis value may be defined as the ratio of plug aperture to tube area) may be done by inserting a series of plugs with different stenosis values. Ultrasound measurements may be made on the downstream tubing, just downstream of the tube, and at differing distances from it, but upstream of the stenosis, to indicate how a spiral form graft will be affected over time by developing atherosclerosis, for example.

For measurement of pulsatile flow, such as blood flow, clearly pulsatile flow conditions can be imposed by control of a pump or a valve. Snapshot and/or time sequence measurements may be made.

Measurement, especially Döppler ultrasound measurement may give, for a tomographic slice of the tubing, a distribution of transverse velocity values against radius from the axis of the tubing. Such a distribution may be analysed by any convenient method. For example, the distribution may be regarded as an image, which may be bit-mapped and subjected to image processing techniques.

For blood flow tubing, which is to say, grafts, whether modified natural or artificial tubing, and possibly also tubing of devices such as heart-lung machines and giving sets, the method according to the Invention indicates that single spiral formation tubing is best, and that downstream stenosis of no more than 44% stenosis value is sufficient to cancel any spiral flow induced by the spiral formation tube—this is rectangular linear profile stenosis. This is already a useful result in terms of aftercare of patients who have received grafts, and indicates that a programme of regular Döppler ultrasound or other measurement of spiral flow in vivo is a useful check on the viability of grafts, not to mention the indication that a graft with a single start thread would be the preferred choice for implantation, whether as an arterial bypass graft or as a leg artery replacement.

The internal spiral formation, in blood flow tubing, may be that of a stent. WO 00/38591 referred to above discloses stents with spiral formations that induce spiral flow in veins or arteries and such slants may also be assessed using the method of the invention. The set-up may be designed to mimic the site at which the stent will be implanted, by suitable choice of tube, and inlet and outlet tubing, and different stents tested, or a reconfigurable stent tested in different configurations, in order to optimise stent performance.

Examples of a method of and apparatus for assessing the effect of a conduit section on flow characteristics of a first fluid in accordance with the invention will now be described with reference to the accompanying drawings, in which.

Figure 1:
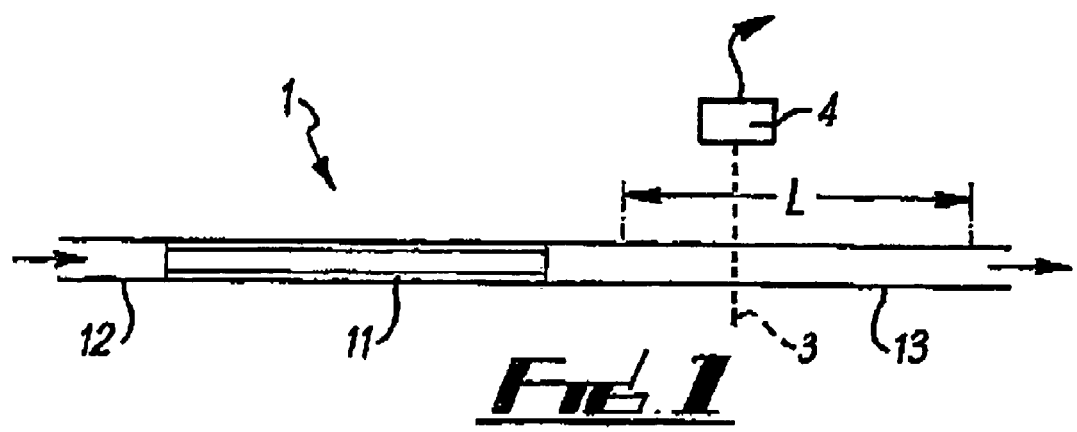
FIG. 1 is a cross-sectional view of a part of a first example of a test system with first examples of upstream tubing and downstream tubing, and a test tube mounted in the test system.

FIG. 1 shows a test tube 11 mounted in a test system 1 between an upstream tubing 12 and a downstream tubing 13.

Figure 2:
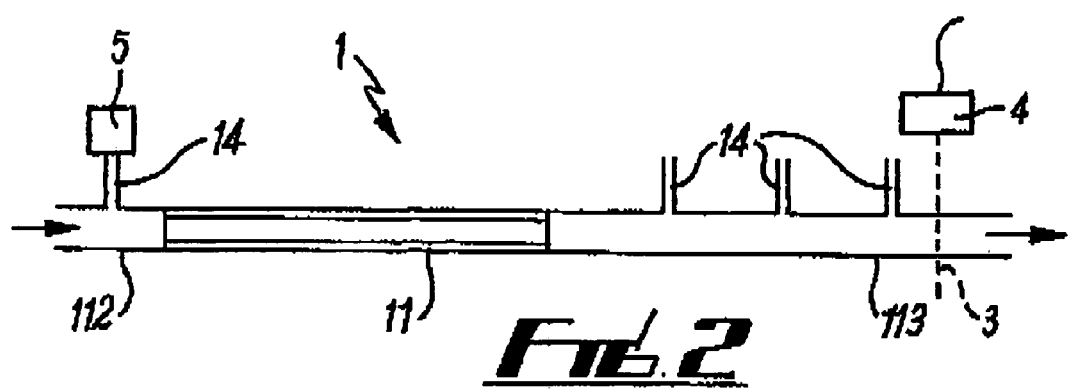
FIG. 2 is a cross-sectional view of the test system with the test tube mounted in the test system, and with second examples of upstream and downstream tubing.

FIG. 2 shows the test system 1 but with an alternative example of upstream tubing 112 and downstream tubing 113. In this example, the tubing 112, 113 has ports 14 which enable the pressure of the fluid in the tubing 112, 113 to be measured.

A Döppler ultrasound probe 4 is located adjacent the downstream tubing 13, 113 of the test system 1 so that transverse flow velocities of fluid in the tube 13, 113 are detected across a plane 3 transverse to the tubing 13, 113. The probe 4 is movable mounted so that it can be moved in a direction parallel to the longitudinal axis of the tubing 13, 113 along the length "L". The Döppler ultrasound techniques enable the range and distribution of transverse foe velocities in the plane to be detected. Döppler ultrasound probes are commercially available, and details will not be elaborated here. Of particular interest is see how spiral flow induced in the tube 11 is maintained downstream, and tomographic slices of fluid are observed at various positions in the downstream tubing 13, 113, within the available length "L".

Although in this example the use of ultrasound is described to detect the transverse flow velocities, any suitable detection system could be used to detect the transverse flow velocities or another suitable transverse flow parameter. An example of another suitable detection system is a magnetic resonance imaging (MRI) system.

The test system 1 also comprises a source for the fluid and pressure means to provide a pressure head in the fluid, neither of which is shown. The pressure means may comprise a fluid reservoir elevated above the tube 11 and/or a pump.

The fluid will usually be a liquid, and a liquid of particular interest is blood, it having been realised that the way blood flows in veins and arteries can have a major influence on the continued patency thereof. WO 00/38591 discusses how spiral formation in blood vessels can prevent build up of deposits on their walls to maintain healthy flow and militate against the formation of clots. Blood could be used for testing, but preferred is a liquid that simulates blood without the problems of maintaining its viability over prolonged tests. A mix of Shelley fluid and ATS mimics blood in terms of density, viscosity and acoustic refractive index, and is ideal for Döppler ultrasound measurements.

Figure 3:
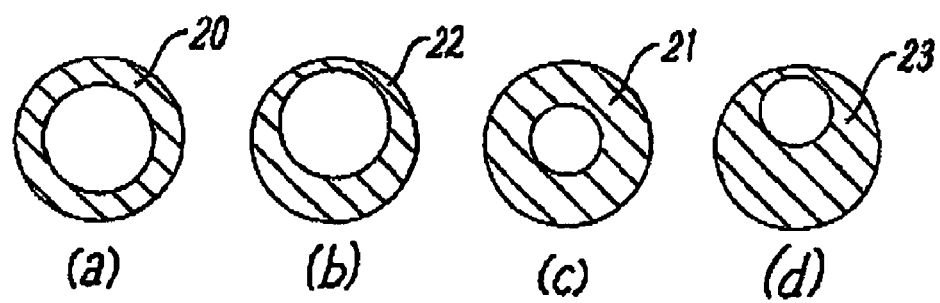
FIG. 3 shows four different stenoses for the measurement mode of FIG. 2.

In addition to the measurement of transverse velocity, it is also considered important to determine how the tube 11 affects pressure in the flow system, and, in particular, how downstream stenosis affects the spiral flow induced by the tube 11. Therefore, the tubing 112, 113 includes pressure sensing ports 14 at various positions in the delivery and receiving tubing 112, 113. The ports 14 each permit a pressure sensor 5 to be coupled to them to permit sensing the pressure at the respective location in the respective tubing 112, 113. Typical testing stenoses are illustrated in FIGS. 3(a) to 3(d) in cross section. FIG. 3(a) and 3(c) show coaxial stenoses 20, 21 respectively, with stenosis values (ratio of hatched blocked area to whole) of 44% and 75% respectively. FIGS. 3(b) and (d) show off-axis stenoses 22, 23 having the same values as the stenoses 20, 21, respectively.

In blood flow tubing, flow is pulsatile, and the flow system is adapted to produce pulsatile flow by suitable motor or vase control. Measurements can be snapshot or continuous over time.

Figure 4:
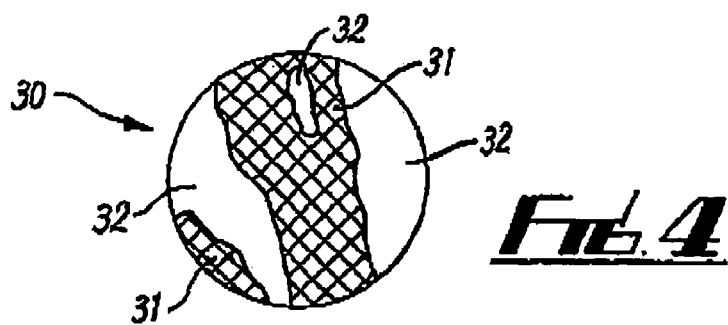
FIG. 4 shows an example of the measurements made by the Döppler ultrasound technique.

FIG. 4 shows a Döppler ultrasound scan 30. These are usually two-colour scans with one colour 31 (hatched area) indlcating flow towards and the other colour 32 (unhatched) indicating flow away from the ultrasound source. The intensity of the colour (which cannot be shown in the drawing) indicates velocity. The scan 30 is generated from output signals output by the probe 4 to a processor 6, which processes the output signals and display them as the scan 30 on an output device 7, such as a visual display.

The processor 6 also processes the output signals using conventional numerical analysis techniques to obtain transverse flow profile, transverse velocity profile, peak transverse velocity and spiral statistical uncertainty. These can then be analysed along with the scan 30 to assess the effect of the test tube 11 in the test system.

The transverse flow profile is an angle corrected velocity $v'(r, \theta)$ which is obtained from the measured velocity $v_{meas}$ and is defined as:

$$v'(r, \theta) = v_{meas}/\sin\theta$$

The transverse velocity profile is the average velocity around a circle of radius r and is defined as:

$$v(r) = \frac{1}{2\pi} \oint v^1(r, \theta) d\theta$$

The peak transverse velocity $v_{peak} \pm \sigma_{peak}$ can be measured from the transverse velocity profile, where:

$$v_{peak} \geq v(r) \forall r$$

$$\sigma_{peak} = \sigma_v(r_{peak}) \text{ where } v(r_{peak}) = v_{peak}$$

The spiral statistical uncertainty S is defined as:

$$S = \frac{1}{Rv_{peak}} \oint \sigma_r(r) dr$$

where R is the internal radius of the test tube 11.

The spiral statistical uncertainty is effectively a percentage of $v_{peak}$. If the spiral statistical uncertainty is greater than 100%, this indicates that no spiral flow was detected. If the spiral statistical uncertainty is less than 100% this indicates that spiral flow was detected. The lower the percentage, the higher the amount of spiral flow detected. Hence, the spiral statistical uncertainty gives an indication of the quality of the spiral flow.

If the peak transverse velocity is low, this indicates that the flow is coherent.

Hence, the peak transverse velocity and the spiral statistical uncertainty provide quantitative indications of the effect of the test tube 11 on fluid flow in the tubing 13, 113.

In addition, if the linear flow characteristic (i.e. the flow parallel to the longitudinal axis of the tubing 13, 113) are also analysed, and a measure is obtained of the peak linear velocity, the ratio of peak transverse velocity to peak linear velocity provides an indication of the speed of travel of the spiral flow along the tubing 13, 113.

The transverse flow profile and the transverse velocity profile can be displayed as graphs and used to proved qualitative indications of the effect of the test tube 11 on the fluid flow in the tubing 13, 113.

The advantage of the scan 30 is that it provides a visual indication of the position and quality of the spiral flow pattern within the tubing 13, 113.

Finally, it is also possible, using the tubing 112, 113 to assess the effect on the test tube 11 on fluid pressures upstream and downstream of the test tube 11. This is important to ensure that the flow pattern produced by the test tube 11 does not have the undesirable side effect of generating fluid pressures that are too high upstream and downstream of the test tube 11.

Figure 5:
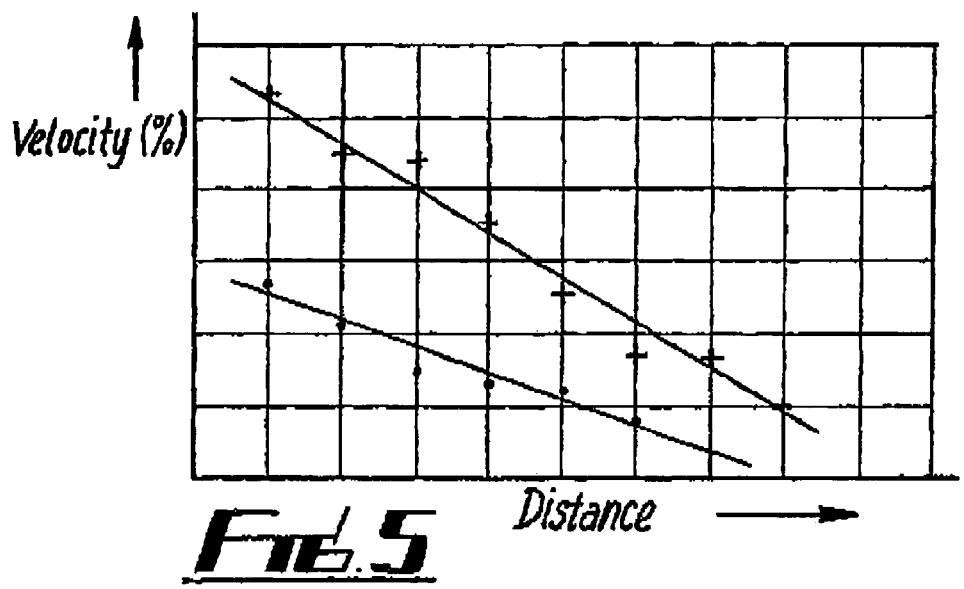
FIG. 5 is a graph showing spiral velocity against distance for two designs of graft.
Figure 6:
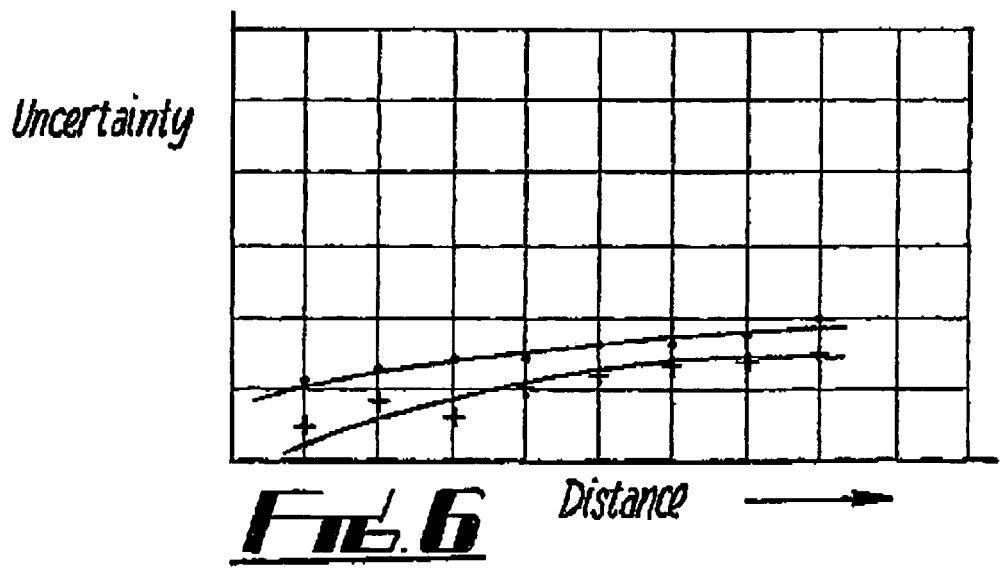
FIG. 6 is a graph showing spiral statistical uncertainty against distance for the two grafts of FIG. 5.
Figure 7:
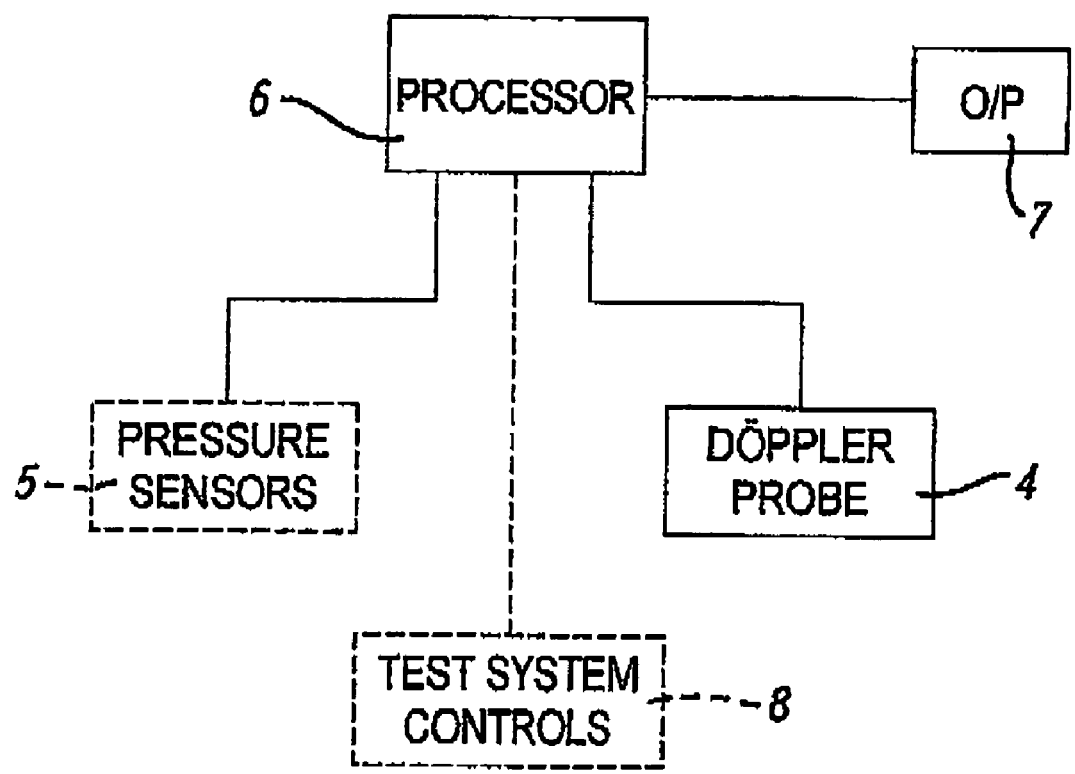
FIG. 7 is a schematic block diagram of the analysing equipment for use with the test systems.

That significant differences between even apparently similar tube configurations can be detected by the method of the invention is demonstrated by reference to FIGS. 5 and 6 which show, for two different grafts, spiral velocity against distance (FIG. 5) and spiral statistical uncertainty against distance (FIG. 6).

Graft 1 was an 8 mm diameter graft with a single internal fin, of helix angle 8°, the depth of the fin being 2 mm. Graft 2 was a similar graft but with two internal fins. It will be seen that the Spiral velocity is higher for Graft 1, and the Spiral statistical uncertainty lower than for Graft 2, indicating that Graft 1 is the better graft, at least by the applied standards.

A flow system according to the invention will have desirably a sufficiently flexible design to accommodate grafts of different lengths and to investigate flow in downstream tubing at different distances, perhaps up to half a metre or more, from the graft under investigation. Fixtures and fittings will be provided facilitating the connection of tube of different diameters and for the insertion of stenoses. For the testing of stents, facilities will be provided for accommodating stents of different designs and for actuating stents which need to be deployed and manipulated in veins and arteries.

In use, the test system 1 can be used to replicate the conditions within an actual flow system by first analysing the flow in the actual flow system and then adjusting parameters of the test system 1 to replicate the actual system. Typical parameters that are analysed and then replicated in the test system 1 are physical properties of the fluid flowing through the test system 1, such as density and viscosity and physical properties of the test system 1, such as fluid pressure, flow velocity and any restrictions within the actual system. The processor 6 can be used to control the test system 1 to emulate the actual system by controlling test system controls 8. Typically, the test system controls 8 can control valves and/or a pump (not shown) in the test system 1.

When the effect of the conduit section 11 on the fluid flow in the test system 1 has been assessed, the effect of the conduit section on fluid flow in be actual system can be derived from the assessment of the effect of the conduit section on flow in the test system 1. The actual system could be any fluid flow system, and especially a system where the fluid is a liquid. For example, the actual system could be an industrial pipeline system, such as an oil or gas pipeline, or a blood vessel system in the human or animal body.

The invention has the advantage that it enables the effect of a conduit section 11 on fluid flow to be assessed in a test system before it is inserted into an actual system. The conduit section 11 may be, for example, designed to improve or after the fluid flow pattern in the actual system. This may be, for example, to reduce turbulence, to alter the wall pressures, to reduce deposits forming within the conduit system and/or to improve flow in the region of a specific conduit geometry, such as a bifurcation or a restriction or enlargement.

The invention claimed is:

1. A method of assessing the effect of a conduit section comprising an internal spiral formation on flow characteristics of a first fluid in a first conduit system, the method comprising:

(a) causing the first fluid to flow through the first conduit system;

(b) detecting a transverse flow parameter of the first fluid in the first conduit system downstream of the conduit section;

(c) determining at least one transverse flow characteristic of the first fluid from the detected transverse flow parameter wherein the at least one transverse flow characteristic comprises peak transverse flow velocity; and (d) assessing the effect of the conduit section from the determined flow characteristics.

2. A method according to claim 1, wherein the transverse flow parameter comprises transverse flow velocity.

3. A method according to claim 2, wherein a number of transverse flow velocities are detected across a cross-section of the first conduit system.

4. A method according to claim 1, wherein the transverse flow parameter is detected using ultrasound.

5. A method according to claim 1, wherein the transverse flow characteristic further comprises spiral statistical uncertainty.

6. A method according to claim 1, wherein the at least one transverse flow characteristic that is determined comprises a qualitative flow characteristic.

7. A method according to claim 6, wherein the qualitative flow characteristic comprises one or more of transverse flow profile and transverse velocity profile.

8. A method according to claim 1, further comprising detecting pressure of the first fluid in the flow system.

9. A method according to claim 8, wherein the pressure is detected downstream of the conduit section.

10. A method according to claim 8, wherein the pressure is detected upstream of the conduit section.

11. A method according to claim 1, further comprising:
 (e) initially analysing flow characteristics of a second conduit system;
 (f) configuring the first conduit system to at least partially emulate the second conduit system; and
 (g) deriving a second assessment of the effect of the conduit section on the flow characteristics of a second fluid in the second conduit system from the assessment of the effect of the conduit section on the flow characteristics of the first fluid in the first conduit system, the first fluid having a known relationship to the second fluid.

12. An apparatus for assessing the effect of a conduit section comprising an internal spiral formation on flow characteristics of a first fluid in a first conduit system, the apparatus comprising:
 (a) a sensing system mounted adjacent to a detecting region of the first conduit system, the sensing system generating an output signal representative of a transverse flow parameter in the detecting region;
 (b) a processor for receiving the output signal and processing the output signal to derive at least one transverse flow characteristic of the first fluid from the output signal wherein the at least one transverse flow characteristic derived by the processor comprises a quantitative flow characteristic, which comprises peak transverse flow velocity; and
 (c) a display device to display the at least one flow characteristic.

13. An apparatus according to claim 12, wherein the sensing system is mounted to detect the transverse flow parameter downstream of the conduit section.

14. An apparatus according to claim 12, wherein the detecting region is a cross-section of the first conduit system.

15. An apparatus according to claim 12, wherein the sensing system comprises a source of ultrasonic waves and a sensor for detecting ultrasonic waves from the detecting region of the first conduit system.

16. An apparatus according to claim 12, wherein the quantitative flow characteristic further comprises spiral statistical uncertainty.

17. An apparatus according to claim 12, wherein the at least one transverse flow characteristic that is determined comprises a qualitative flow characteristic.

18. An apparatus according to claim 17, wherein the qualitative flow characteristic comprises one or more of transverse flow profile and transverse velocity profile.

19. An apparatus according to claim 12, further comprising a pressure sensor to detect the pressure of the first fluid in the first conduit system.

* * * * *